United States Patent [19]

Lipson

[11] Patent Number: 4,511,225
[45] Date of Patent: Apr. 16, 1985

[54] VARIABLE NEUTRAL DENSITY LASER GOGGLES

[76] Inventor: Herbert G. Lipson, 68 Aldrich Rd., Wakefield, Mass. 01880

[21] Appl. No.: 452,600

[22] Filed: Dec. 23, 1982

[51] Int. Cl.³ .............................................. G02C 7/12
[52] U.S. Cl. ...................................... 351/49; 351/47; 2/432
[58] Field of Search ................. 351/44, 47, 49; 2/431, 2/432, 433; 350/407

[56] References Cited

U.S. PATENT DOCUMENTS

| | | | |
|---|---|---|---|
| 2,409,356 | 10/1946 | Hutchings | 88/54 |
| 2,422,287 | 6/1947 | Bernheim et al. | 351/49 |
| 2,887,010 | 5/1959 | Ruettiger | 88/112 |
| 3,267,807 | 8/1966 | Swope et al. | 88/112 |
| 3,519,339 | 7/1970 | Hutchinson et al. | 351/44 |
| 3,781,089 | 12/1973 | Fay et al. | 350/164 |
| 4,119,369 | 10/1978 | Eloranta et al. | 351/47 |
| 4,202,601 | 5/1980 | Burbo et al. | 351/49 |

Primary Examiner—John K. Corbin
Assistant Examiner—Paul Dzierzynski
Attorney, Agent, or Firm—Donald J. Singer; Stanton E. Collier

[57] ABSTRACT

Continuously variable neutral density laser goggles are worn by a user so as to enable the user to align and focus laser beams of specified wavelength. A laser goggles frame has the eye openings adapted to receive filter units therein having three polarized elements, two fixed and one rotatable by an external adjusting lever, that vary in absorbance at the specified wavelength. A connecting rod is connected to each of the adjusting levers so that movement of the connecting rod causes identical movement of the rotatable elements. Additional filter units can be stacked and connected to provide additional absorption when necessary. The user of the goggles firstly maximizes absorption after which the area of concern is observed. The amount of absorption is slowly reduced by moving the connecting rod until the laser radiation is barely visible. Additional filters can be added that eliminate invisible radiation and transmit only visible radiation. In combination with the above, this allows viewing of interaction area when $CO_2$ laser is used in laser welding.

2 Claims, 7 Drawing Figures

VARIABLE NEUTRAL DENSITY LASER GOGGLES

STATEMENT OF GOVERNMENT INTEREST

The invention described herein may be manufactured and used by or for the Government for governmental purposes without the payment of any royalty thereon.

BACKGROUND OF THE INVENTION

This invention relates generally to means for protecting human eyes from laser radiation, and, more particularly, to variable neutral density laser goggles.

The application of these goggles is to protect the wearer's eyes from intense radiation scattered or reflected from optical elements in the beam path of laser or other optical systems utilizing extremely bright light sources. They are not intended for direct viewing of laser beams. In the past, protection from laser radiation of a given wavelength was adequately provided for by laser goggles having filters therein that selectively removed the given wavelength of laser radiation. These goggles are so effective that one is almost unable to see the laser beam when it is reflected off an opaque surface.

A problem arises when one tries to align optical elements or focus beams using the actual laser beam with the above laser goggles. If one is hardly able to see the beam, alignment or focusing is almost impossible and one has the unsafe urge to remove the laser goggles. One answer to this problem is the stacking of neutral density filters. This method of removing or adding filters is inconvenient, time consuming and may lead to dangerous errors in reducing the laser radiation to safe observable levels when the laser must be adjusted over a wide range of intensities.

In the case of carbon dioxide laser welding, the laser beam is invisible and only the area of interaction with the metals is visible because of heating. If one only wears laser goggles that filter out the dangerous invisible $CO_2$ laser radiation but allows visible radiation to pass, one is hardly able to directly view the interaction area because of the high intensity of the visible radiation emitted. The answer to this problem in the past required the combination of an invisible laser radiation filter with stacking of neutral density filters to lower the intensity of visible radiation as well as remove the invisible laser radiation.

The present invention is directed toward providing variable neutral density laser goggles in which these undesirable characteristics are minimized.

SUMMARY OF THE INVENTION

The present invention overcomes the problems encountered in the past and described hereinabove by providing variable neutral density laser goggles which are capable of adjustment in absorbance.

A conventional laser goggles frame is adapted to receive a plurality of polarizer filter units in each eye opening. Each polarizer filter unit is capable of continuous adjustment in the relative absorption over a given wavelength. These units may be stacked to form a set so that higher power laser beams may also be observed and are further coupled to each connected unit for cooperative adjustment. Further, each set in the left and right eye openings are cooperatively connected by mechanical means, for example, so that the user may easily adjust both sets because of variations in the laser beam intensity. Initially, the user of the variable neutral density laser goggles moves a control means so that the amount of absorbance is at the maximum. The user then looks at the area of concern and then reduces the amount of absorbance until the laser beam is visible.

When one is working near invisible laser radiation, $CO_2$ laser welding, for example, a visible transmitting high optical density ultraviolet or infrared filter is attached to the filter unit in each eye position. Therefore, the invisible laser radiation is removed and the variable neutral density units can be adjusted to reduce the intensity of the visible radiation. In this manner, the invisible laser beam can be focused by observing the interaction area of concern.

It is therefore one object of this invention to provide for laser goggles having variable neutral density materials in each eye opening.

It is a further object of this invention to provide for laser goggles having stackable variable neutral density units in each eye opening.

It is still a further object of this invention to provide for laser goggles having stackable variable neutral density units wherein each unit of each stack moves in cooperation with other units of that stack.

It is another object of this invention to provide for laser goggles having stackable units forming a set in each eye opening wherein each set moves in cooperation with the other set.

And it is still another object of this invention to provide for laser goggles having invisible laser radiation filters and stackable variable neutral density units therein.

These and many other objects and advantages of the present invention will be readily apparent to one skilled in the pertinent art from the following detailed description of a preferred embodiment of the invention and related drawings.

DETAILED DESCRIPTION OF THE PREFERRED EMBODIMENT

Figure 1:
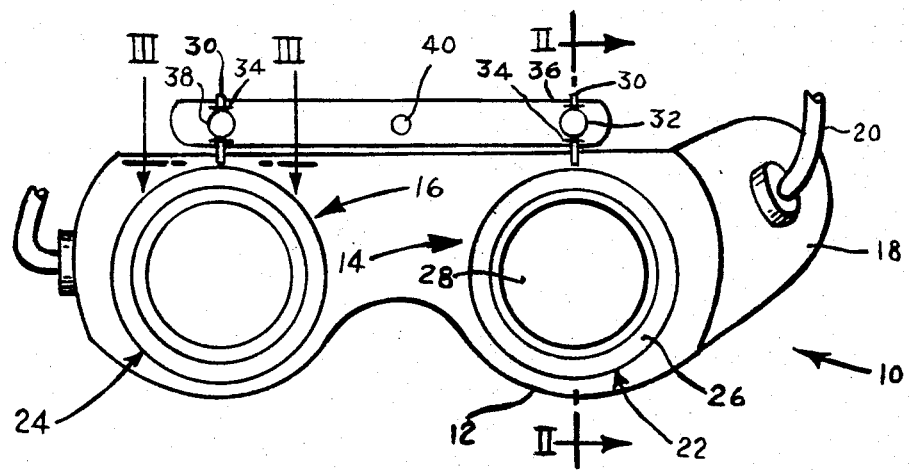
FIG. 1 is a front view of the laser goggles of this invention.

Referring to FIG. 1, laser goggles 10 of this invention is pictorially illustrated. A conventional laser goggles frame 12 made of opaque plastic has a left and a right eye opening 14 and 16, respectively, with two blinders 18, only one shown, attached to the front of frame 12. Other blinders on top and bottom are not shown. A headstrap 20, only partially shown, is attached to blinders 18. The blinders in cooperation with frame 12 prevent stray laser radiation from entering the eyes of the user from the rear, top or bottom direction by being closely fitting to the face of the user. The frame is held closely in place by strap 20.

A left and a right variable neutral density filter units 22 and 24, respectively, are attached to frame 12 by conventional means such as threaded fittings or retaining rings, not shown. Further explanation of filter units will refer to left filter unit 22 only since both filter units 22 and 24 are the same, unless otherwise stated. Filter unit 22 has a housing 26 for holding a filter medium 28, and an adjusting lever 30 with conventional means for selectively turning components of filter medium 28. Filter medium 28, first adjusting lever 30 and conventional means of selectively turning are shown in Oriel, Inc., Model 2860 polarizer. This polarizer has three elements that filter out wavelengths from 450 to 790 micrometers.

Figure 2:
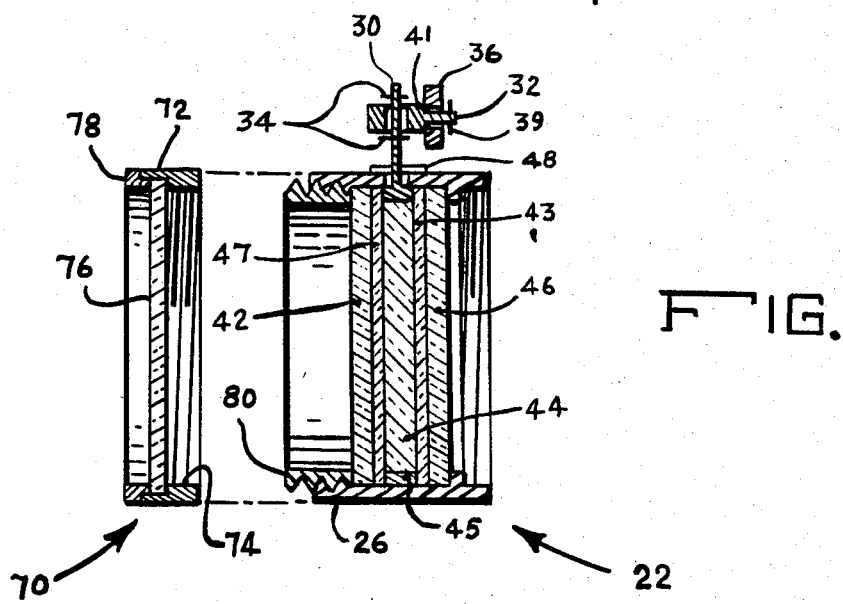
FIG. 2 is a cross section taken along lines II—II of FIG. 1 excluding the frame and showing one of the variable neutral density filter units with connecting means of this invention and an invisible laser radiation filter for connecting to the filter unit shown.

Although not shown in FIG. 1, an additional invisible radiation filter 70, shown in FIG. 2, can be attached to filter units 22 and 24 to filter out invisible laser radiation, in the ultraviolet or infrared region, for example, but allows visible radiation to pass.

Adjusting lever 30 is fixedly attached to pivot 32, one of two, by means of c-clips 34. A connecting rod 36 has pivots 32 and 38 rotatably mounted therein so that when a second adjusting lever 40, fixedly attached to connecting rod 36, is moved either right or left, the amount of absorbance of laser radiation changes in filter units 22 and 24 in unison.

Figure 3:
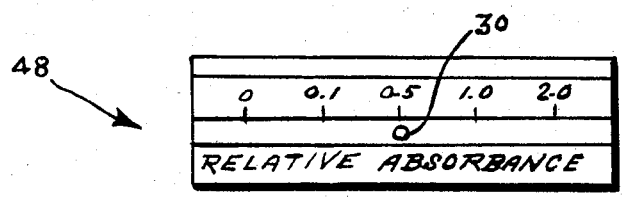
FIG. 3 is a top view of one of the variable neutral density filter units taken along lines III—III of FIG. 1 showing an absorbance scale attached to a housing of the filter unit.

In order to understand the relationship between filter unit 22 and connecting rod 36, a cross section along lines II—II is shown in FIG. 2. One embodiment of filter medium 28 is that noted above manufactured by Oriel, Inc. As shown in FIG. 2, three polarizers 42, 44 and 46 and two separating sheets 43 and 47 are mounted in housing 26 of filter unit 22 so that external polarizers 42 and 46 are fixed and have parallel planes of polarization while internal polarizer 44 is rotatable. Internal polarizer 44 is fixedly mounted in an annular ring 45 that has adjusting lever 30 fixedly secured thereto. In the concerned wavelength range from about 450 to 790 micrometers, the amount of absorbance is illustrated by FIG. 3 which is a top view of a scale 48 attached to housing 26. By turning polarizer 44 by adjusting lever 30 allows selection of absorbance from 0 to 2.0 when one filter unit 22 is used in each eye opening 14 and 16.

FIG. 3 also illustrates the manner of connecting adjusting lever 30 to connecting rod 36. Pivot 32 has a transverse hole therethrough into which adjusting lever 30 is inserted and held in place by two c-clips 34. Connecting rod 36 has a hole therethrough into which one end of pivot 32 is inserted and is held in place by a c-clip 39 and a shoulder 41 on pivot 32. A left or right movement of connecting rod 36 causes pivot 32 to rotate in rod 36 as adjusting lever 30 is rotated about a longitudinal axis of filter unit 22.

Stacking of filter units 22 causes absorbance scale 48 to be nonapplicable to total transmisson. At maximum absorption, filter unit 22 transmits only about 0.1% of the laser radiation at a value of 2.0. Other filter media can be selected to absorb other laser radiation wavelengths. Also, other polarizer arrangements are within the scope of the invention if the absorption is sufficiently high in the concerned wavelengths.

Invisible radiation filter 70, illustrated in cross section in FIG. 2, is removably attachable to the male threaded section of a retaining ring 80 of filter unit 22 by a female threaded section 74 of a filter housing 72. An invisible radiation filter medium 76 that allows visible radiation to pass is fixedly held in filter housing 72 by a pressure ring 78. The construction of invisible radiation filter 70 is conventional. Invisible radiation in the ultraviolet and infrared region is of particular concern because of damaging effects to the eyes. This type of radiation occurs, for example, in $CO_2$ laser welding.

Although the present invention is primarily concerned with visible wavelength laser radiation, the principles are clearly applicable if nonvisible wavelengths can be made observeable through imaging devices associated with laser goggles 10. The principle area of application of the present invention is associated with aligning and focusing laser beams.

Figure 6A:
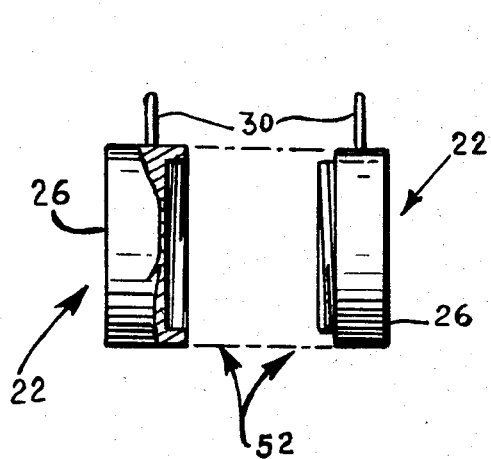
FIG. 6a illustrates by side view one manner of connecting two variable neutral density units in one stack.

In very high power laser operations, a plurality of filter units 22 can be stacked to produce even greater absorption at concerned wavelengths. Referring to FIG. 6a, this illustrates a means for coupling housing 26 of filter units 22 to form a stacked set 50 shown in FIG. 6b. The means illustrated are a conventional pair of male and female threaded fittings 52.

Figure 6B:
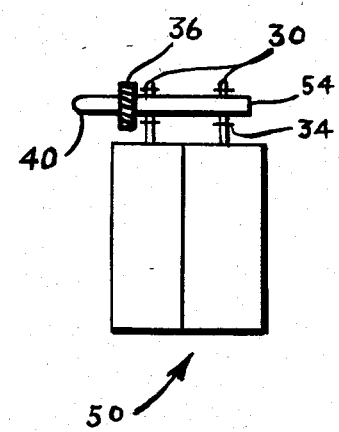
FIG. 6b illustrates by side view one possible manner of cooperatively coupling two variable neutral density units in a stack of the laser goggles of FIG. 1.

FIG. 6b illustrates a possible means of coupling a plurality of adjusting levers 30 in stacked set 50. An extended pivot 54 is similar to pivot 32 of FIGS. 1 and 2 except that a plurality of holes are drilled therethrough so that adjusting levers 30 can be mounted therein and held therein by c-clips. Identical reference numbers are used in the various figures to identify identical elements.

Figure 4:
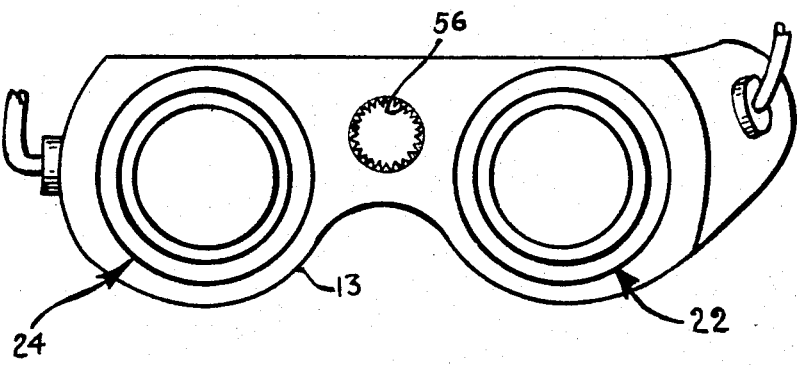
FIG. 4 illustrates by front view an alternative version of the laser goggles of this invention.
Figure 5:
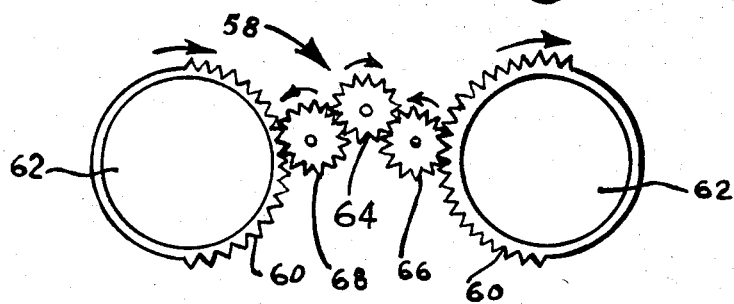
FIG. 5 is a pictorial representation of one possible means for gearing variable neutral density units together.

The alternative coupling means for filtering units 22 and 24 is illustrated in FIGS. 4 and 5. In FIG. 4 an adjusting knob 56 having a grooved outer surface is connected to a center spur gear 64, shown in FIG. 5. A plurality of spur gears 58 are connected to two geared sectors 60 having rotatable polarizer medium 62 attached therein. By turning adjusting knob 56 clockwise, for example, causes center spur gear 64 to turn intermediate spur gears 66 and 68 counterclockwise and rotate polarizer medium 62 clockwise thus causing parallel movement of the polarized planes therein. Other arrangements of gears are clearly possible to achieve the same effect.

A stacking is also possible using an alternative coupling means. This is achieved when the left and right filter units 22 and 24 and gearing shown in FIG. 5 are encased as a single unit. The encased unit is connected to frame 13 by conventional means. An adjusting knob would have a rear portion, not shown, that would fit closely over the grooved outer edge of adjusting knob 56 so that when an outer adjusting knob is turned all other adjusting knobs are turned in unison.

In using the laser goggles 10 of the present invention when only visible radiation is present, the user attaches the laser goggles 10 to his head by head strap 20 and moves connecting rod 36, FIG. 1, to obtain maximum absorbance. The user then observes the point of interest and decreases the amount of absorbance until a safe level is obtained. If invisible laser radiation is present, the user attaches one filter to each filter unit, 22 and 24, for example. Filter 70 eliminates the danger of invisible laser radiation, but allows visible radiation to pass. As noted above, the user can adjust the absorbance to a safe level when viewing visible radiation.

One example of use occurs during $CO_2$ laser welding. The laser beam output is invisible but the area of interaction may appear very bright. If only filter 70 is used, the user has no way of reducing the intensity of the visible light emitted from the area of interaction. By combining filter 70 with filter units 22 and 24 allows maximum safety by eliminating invisible radiation and reducing visible radiation to a safe level.

Clearly, many modifications and variations of the present invention are possible in light of the above teachings and it is therefore understood, that within the inventive scope of the inventive concept, the invention may be practiced otherwise than specifically claimed.

What is claimed is:

1. Variable density laser goggles comprising:
   a frame made of laser opaque material having a left and a right eye opening therein, said frame preventing laser radiation from entering into a user's eyes except through eye openings;
   means for holding said frame to the user's head;
   a plurality of variable density filter units removably secured to said frame in said eye openings, each of said filter units having a housing with means for removable attachment to said frame, means for removable attachment to another of said filter units, and for removable attachment to a laser filter for invisible radiation, said filter units having a three element polarizer mounted in said housing, and means for varying the absorbance of said polarizer, said three element polarizer providing an extended rotation adjustment range such that a user is able to precisely select a given absorbance without excessive attempts;
   means for coupling said filter units in each of said eye openings wherein the amount of absorbance in each eye opening is substantially equal; and
   means for filtering out invisible laser radiation removably attached to said filter units.

2. Variable density laser goggles as defined in claim 1 wherein said means for coupling said filter units comprises
   a pivot for fixedly holding each of said means for varying the absorbance of said filter units, said pivot having at least one hole perpendicular to a longitudinal axis of said pivot, said hole receiving an adjusting lever of said filter unit and being held in said hole by clipping means, said adjusting lever connected fixedly to said three element polarizer of said filter unit, said pivot further including means for connecting said means for varying the absorbance of a plurality of filter units stacked together to form a set; and
   a connecting rod having means for rotatably securing on opposite ends of said rod two of said pivots, whereby lateral movement of said connecting rod cause rotation of said adjusting levers connected to said pivots.

* * * * *